US008920397B2

(12) United States Patent
Sabbagh

(10) Patent No.: US 8,920,397 B2
(45) Date of Patent: Dec. 30, 2014

(54) STATIC AND STABLE FEMININE HYGIENE PAD WITH RELEASABLE ATTACHMENT

(76) Inventor: Jimmy El Sabbagh, Lady Lake, FL (US)

(*) Notice: Subject to any disclaimer, the term of this patent is extended or adjusted under 35 U.S.C. 154(b) by 155 days.

(21) Appl. No.: 13/446,953

(22) Filed: Apr. 13, 2012

(65) Prior Publication Data

US 2013/0274698 A1    Oct. 17, 2013

(51) Int. Cl.
*A61F 13/15* (2006.01)
*A61F 13/47* (2006.01)
*A61F 13/62* (2006.01)

(52) U.S. Cl.
USPC ............ 604/385.03; 604/385.04; 604/385.31

(58) Field of Classification Search
CPC ............ A61F 13/4702; A61F 13/5611; A61F 13/5616
USPC ............... 604/385.03, 385.04, 386, 387, 391, 604/385.31
See application file for complete search history.

(56) References Cited

U.S. PATENT DOCUMENTS

| | | | |
|---|---|---|---|
| 5,221,275 A * | 6/1993 | Van Iten | 604/387 |
| 5,388,275 A | 2/1995 | Oram | |
| 5,415,650 A | 5/1995 | Sigl | |
| 5,704,931 A * | 1/1998 | Holtman et al. | 604/387 |
| 5,778,457 A | 7/1998 | Conway | |
| 5,779,691 A * | 7/1998 | Schmitt | 604/386 |
| H0001788 H * | 2/1999 | Christon et al. | 604/385.101 |
| 6,029,281 A | 2/2000 | Battley | |
| 6,093,178 A * | 7/2000 | Osborn et al. | 604/387 |
| 6,350,257 B1 | 2/2002 | Björklund et al. | |
| 6,616,649 B1 | 9/2003 | Ismail | |
| 6,632,207 B2 | 10/2003 | Rangel et al. | |
| 7,444,722 B2 | 11/2008 | McDaniel et al. | |
| 7,805,768 B2 | 10/2010 | Martz | |
| 2003/0199842 A1* | 10/2003 | Luizzi et al. | 604/385.02 |
| 2005/0131372 A1* | 6/2005 | Wheeler et al. | 604/385.04 |
| 2008/0221542 A1 | 9/2008 | Zhao et al. | |
| 2009/0062761 A1 | 3/2009 | Goerg-Wood et al. | |
| 2010/0087793 A1* | 4/2010 | Magnusson et al. | 604/359 |
| 2010/0095436 A1 | 4/2010 | Giles | |
| 2010/0179500 A1* | 7/2010 | Roe et al. | 604/385.14 |

FOREIGN PATENT DOCUMENTS

| | | | |
|---|---|---|---|
| CA | 2488583 A1 * | 6/2005 | |
| EP | 0 276 970 A2 | 8/1988 | |
| MX | 2011009201 A | 9/2011 | |
| WO | WO 2010004322 A1 * | 1/2010 | |
| WO | WO 2010101502 A1 * | 9/2010 | |

* cited by examiner

*Primary Examiner* — Tan-Uyen (Jackie) T Ho
*Assistant Examiner* — Kathryn E. Ditmer
(74) *Attorney, Agent, or Firm* — Richard C Litman

(57) ABSTRACT

A feminine hygiene pad with releasable attachment is a conventional feminine hygiene pad having an absorbent upper layer and a liquid impermeable lower layer, at least one elastic element attached to the lower layer to maintain the feminine hygiene pad in a non-collapsed state, and a pair of releasable attachments (fasteners) for releasably securing the lower layer to an inner surface of an undergarment. The pair of releasable attachments are formed from just the hook portions of hook and loop fasteners, and are attached to respective longitudinally opposed ends of the lower layer. The material forming the undergarment, such as cotton or the like, acts as a corresponding loop portion for releasable securement thereto.

13 Claims, 3 Drawing Sheets

STATIC AND STABLE FEMININE HYGIENE PAD WITH RELEASABLE ATTACHMENT

BACKGROUND OF THE INVENTION

1. Field of the Invention

The present invention relates to absorbent articles, and particularly to a feminine hygiene pad with a releasable attachment for releasable securement to undergarments.

2. Description of the Related Art

A feminine hygiene pad (also commonly referred to as a sanitary napkin, sanitary pad or menstrual pad) is an absorbent item worn by a woman while she is menstruating, recovering from vaginal surgery, for lochia (i.e., post-birth bleeding), or any other situation where it is necessary to absorb a flow of blood from a woman's vagina. The feminine hygiene pad is worn externally, between the vulva and a woman's undergarment.

The length, size, and shape of feminine hygiene pads vary greatly, due to a wide variety of uses, body types, undergarment styles and sizes, and personal preference. Other options are often offered in a manufacturer's line of pads, such as wings or tabs that wrap around the sides of the woman's underwear to add additional leak protection and help secure the pad in place. Although absorbency and comfort are primary concerns in the manufacture and use of feminine hygiene pads, the overall stability and stable positioning of the pad is also of great concern.

Due to movement of the body during sleep, exercise, or simply through walking or shifting one's weight, a feminine hygiene pad can shift position within the undergarment, thus decreasing the level and scope of protection of the undergarment from leakage. Further, such movements may also cause the pad, which is typically manufactured to be as lightweight, thin and flexible as possible, to fold, bunch or otherwise deform within the undergarments, thus causing discomfort for the user and further decreasing the scope of protection of the undergarment from leakage. Although the use of adhesives to maintain the position of a pad within the undergarment is known, such adhesive attachments may be difficult for the user to apply to undergarments when time and space are constrained, such as in a public bathroom, and can further damage the undergarment with a sticky adhesive residue. Adhesives are also often not strong enough to maintain the pad in place for extended periods of time, or under the added conditions of body heat and perspiration.

Thus, a static and stable feminine hygiene pad with a releasable attachment, and further with static bands, solving the aforementioned problems is desired.

SUMMARY OF THE INVENTION

The feminine hygiene pad with releasable attachment is a conventional feminine hygiene pad having an absorbent upper layer and a liquid impermeable lower layer, and has at least one elastic element secured to the lower layer to maintain the feminine hygiene pad in a non-collapsed state, and a further pair of releasable attachments for releasably securing the lower layer to an inner surface of an undergarment. The pair of releasable attachments are formed from just the hook portions of hook and loop fasteners, and are secured to respective longitudinally opposed ends of the lower layer. The material forming the undergarment, such as cotton, polyester, cotton/polyester blends or the like, acts as a corresponding loop portion for releasable securement thereto. In order to maximize comfort for the user, the releasable attachments are very thin, preferably on the order of a millimeter in thickness or less.

Preferably, a pair of tabs are provided, each tab having a free end and a fixed end. The fixed ends are rigidly attached to the lower layer of the feminine hygiene pad adjacent the longitudinal ends thereof, and the pair of hook portions are mounted on the pair of tabs. In addition to the releasable attachment of the pair of tabs to the undergarment, a secondary hook portion may be provided for direct releasable securement between the lower surface and the undergarment, the secondary hook portion being secured to the lower surface substantially central thereto. As an alternative, the releasable fasteners may be secured to the lower layer of the pad with little or no movement or adjustment with respect to the pad. The at least one elastic element is preferably positioned adjacent the secondary hook portion, and multiple such elastic elements may sandwich or at least partially surround the secondary hook portion. It should be understood that the present hygiene pad may be used for other purposes. Although the use of hygiene pads for menstruation is common, the present pad may also be utilized for incontinence, bladder leakage, or any other purpose or situation in which absorbent hygienic pads and/or garments are used. Additionally, it should be understood that the present pad may be used in combination with diapers, panty liners and the like.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
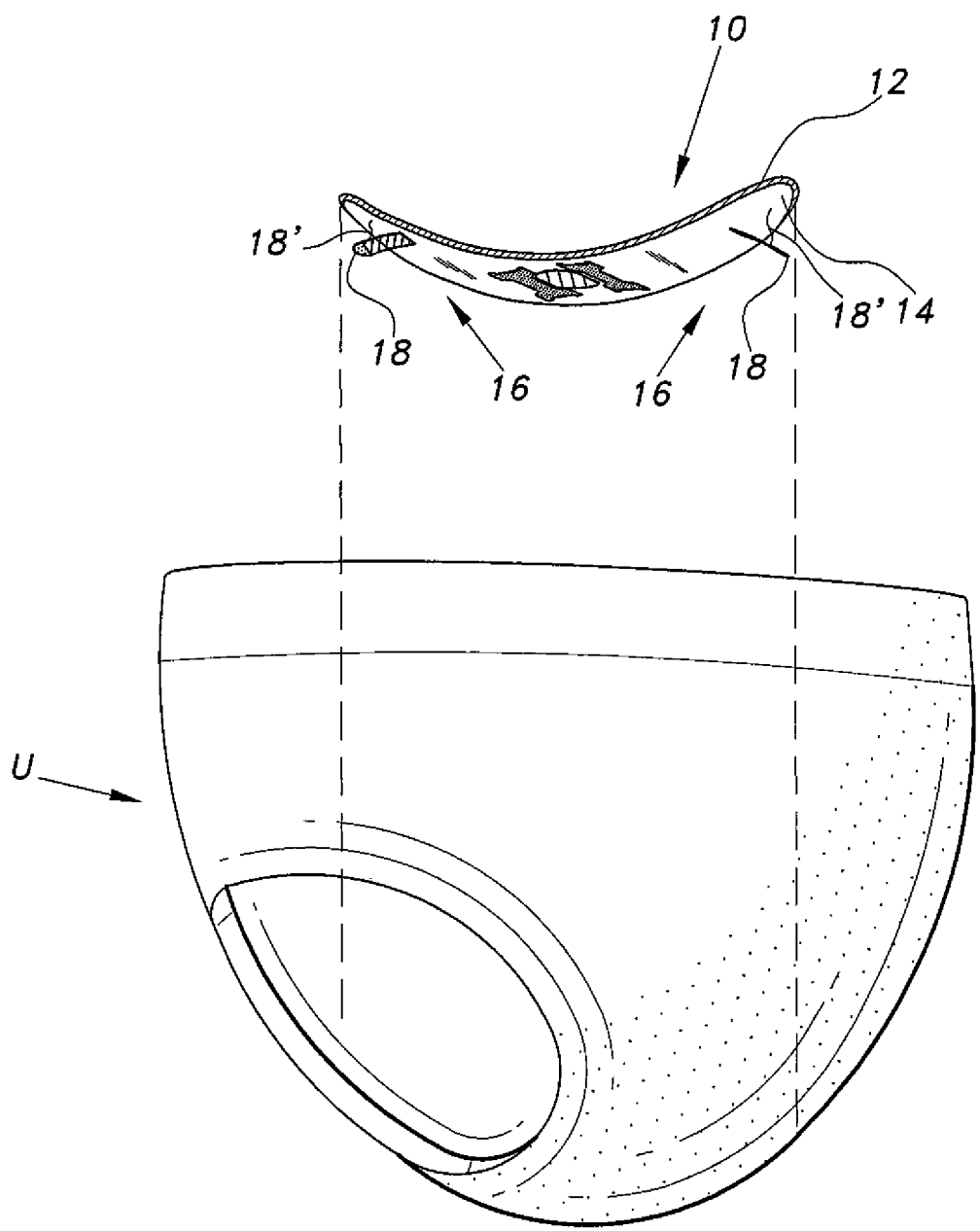
FIG. 1 is an environmental, perspective view of a feminine hygiene pad with releasable attachment according to the present invention.
Figure 2:
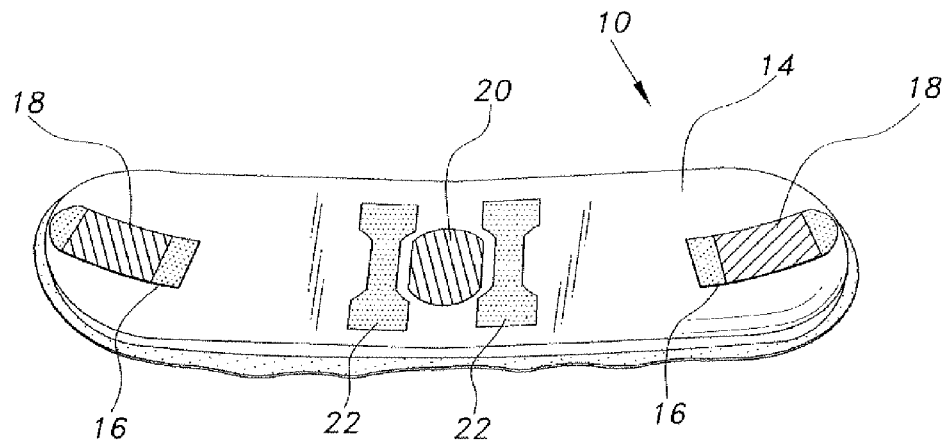
FIG. 2 is a perspective view of the feminine hygiene pad with releasable fastener of FIG. 1.

As shown in FIGS. 1 and 2, the feminine hygiene pad with releasable attachment, designated generally as 10 in the drawings, is a conventional feminine hygiene pad having an absorbent upper layer 12 and a liquid impermeable lower layer 14, and at least one elastic element 22 secured to the lower layer 14 to maintain the feminine hygiene pad 10 in a non-collapsed state, and a pair of releasable attachments (fasteners) 18 for releasably securing the lower layer 14 to an inner surface of an undergarment U.

The elastic elements 22 may be formed from any suitable resilient and/or elastic material, and may be secured to the lower layer 14 by any suitable method, such as adhesives, stitching or the like. The elastic elements 22, for example, may be formed from materials such as that commonly used in nasal strips, such as that taught by U.S. Pat. No. 6,357,436 and sold under the mark Breathe Right®, manufactured by GlaxoSmithKline, LLC of Delaware. It should be understood that the elastic elements 22 may be any suitable type of resilient bands, and preferably are relatively thin, along the order of 1 millimeter wide and 1 millimeter or less in thickness, and may be used singly or formed into structures composed of multiple such individual bands. Alternatively, elastic elements 22, as will be described below, may have any desired size, shape or configuration.

In the preferred embodiment, best seen in FIG. 2, a pair of tabs 16 are provided, each tab 16 having a free end and a fixed end. The fixed ends arc rigidly attached to the lower layer 14 of the feminine hygiene pad 10 adjacent the longitudinal ends thereof. The fixed end may be secured to the lower layer 14 by any suitable means of permanent attachment, such as stitching, adhesives, heat sealing or the like. The tabs 16 may be formed of an elastomeric material, allowing for a small degree of stretching and adjustment. It should be understood that the configuration of tabs 16 may be varied. As one alternative, each tab 16 may be fixed at both ends, thus securing both ends of each tab 16 to the lower layer 14. This could be used to firmly secure the releasable attachments 18, or to give them slight positional adjustability. As a further alternative, one end may remain free, but movement, rotation and extension thereof may be limited by the addition of a tethering piece of material 18', on the order of a quarter of an inch in length, for example. It should be understood that the tethering, which ultimately controls the positional adjustability of the free end, may be varied, dependent upon the needs and desires of the user. Preferably, any tethering material and the material used to form tabs 16 are selected to optimize comfort for the user, being thin, flexible and preferably formed from a comfortable material, such as the elastomeric or elastomeric mesh material commonly found in the manufacture of infant diapers.

Releasable attachments 18 are secured to the tabs 16, as best shown in FIG. 2, for releasably securing the tabs 16 (and lower layer 14) to the inner surface of an undergarment U. Preferably, releasable attachments 18 are formed from just the hook portions of hook and loop fasteners. The material forming the undergarment itself, such as cotton or the like, acts as a corresponding loop portion for releasable securement thereto, i.e., loose fibers and fiber ends of the material itself act as a corresponding loop portion, permitting releasable attachment of the hook portions 18 to the undergarment U. It should be understood that the releasable attachments 18 are very thin, along the order of 1 millimeter or less, in order to optimize comfort for the user.

Figure 5:
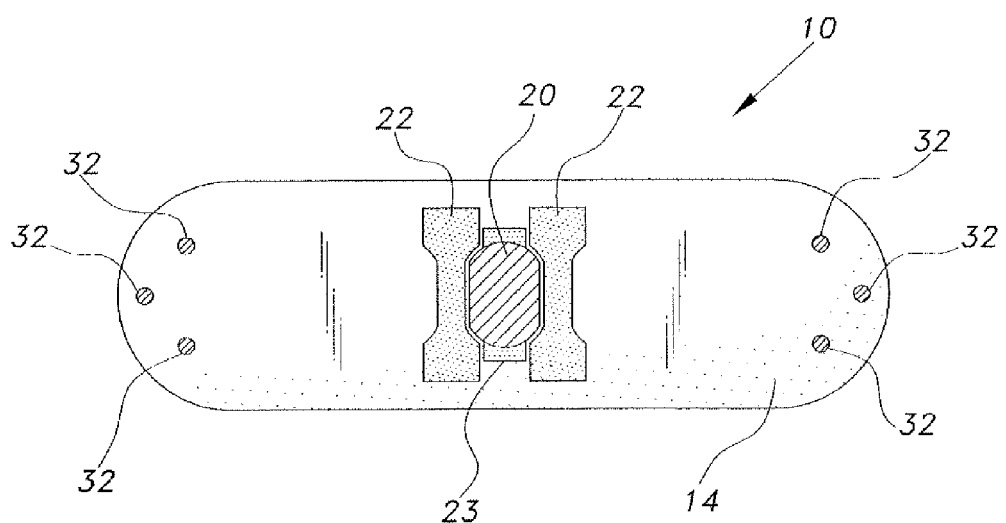
FIG. 5 is a plan view of a still further alternative embodiment of a feminine hygiene pad with releasable fastener according to the present invention.

It should be understood that the size, overall configuration, and number of releasable attachments 18 may be varied according to the dimensions and configuration of the hygiene pad and conditions of use. In the alternative embodiment of FIG. 5, the tabs 16 have been removed and the releasable attachments 32 have been secured directly to the lower surface 14 of feminine hygiene pad 10. The releasable attachments 32 may be secured thereto (or, alternatively, to tabs 16) by any suitable form of permanent attachment, such as stitching or the like. In FIG. 5, the releasable attachments 32 are shown as being substantially circular and grouped in sets of three. It should be understood that the relative dimensions, configuration, number, and positioning of the releasable attachments 32 are shown in FIG. 5 for exemplary purposes only, and that the relative dimensions, configuration, number, and positioning of the releasable attachments may be varied.

Returning to the preferred embodiment of FIGS. 1 and 2, in addition to the releasable attachment of the pair of tabs 16 to the undergarment U, a secondary hook portion 20 may be provided for direct releasable securement between the lower surface 14 of the pad 10 and the undergarment U. Preferably, the secondary hook portion 20 is attached to the lower surface 14 substantially central thereto, as shown, although it should be understood that the relative dimensions, configuration, number, and positioning of the secondary hook portion 20 may also be varied.

The at least one elastic element 22 is preferably positioned adjacent the secondary hook portion 20. As shown in FIG. 2, a pair of elastic elements 22 are provided and sandwich the secondary hook portion 20. Similar to the secondary hook portion 20, it should be understood that the relative dimensions, configuration, number, and positioning of the elastic element(s) 22 may be varied. In the alternative embodiment of FIG. 3, an integral peripheral elastic element 28 is provided, substantially surrounding the central secondary hook portion 20. In the further alternative embodiment of FIG. 4, the entire lower layer 14 of the feminine hygiene pad 10 is substantially covered by a large elastic element 30 for maintaining the feminine hygiene pad 10 in a non-collapsed state. The size and configuration of the large elastic element 30, as noted above, may be varied, and, as a further alternative, cooling and drying apertures may be formed therethrough, as is known in the construction of the lower layers of feminine hygiene pads. In FIG. 4, a central hook portion 20 and longitudinally opposed auxiliary hook portions 21 are further provided, which are attached to the elastic portion 30. The hook portions 21 are shown as having relatively thin crescent shapes, though it should be understood that the overall configuration and relative dimensions of the auxiliary hook portions 21 may be varied.

Figure 3:
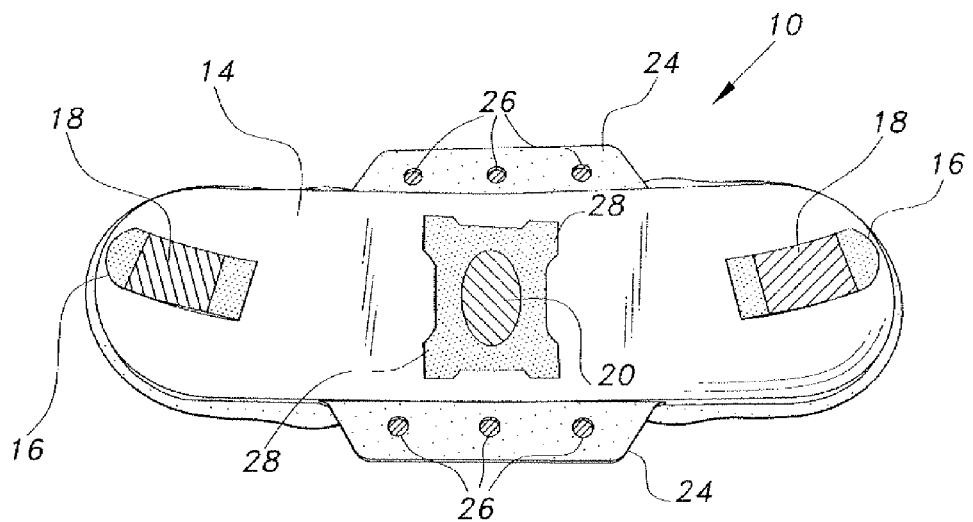
FIG. 3 is a perspective view of an alternative embodiment of a feminine hygiene pad with releasable fastener according to the present invention.
Figure 4:
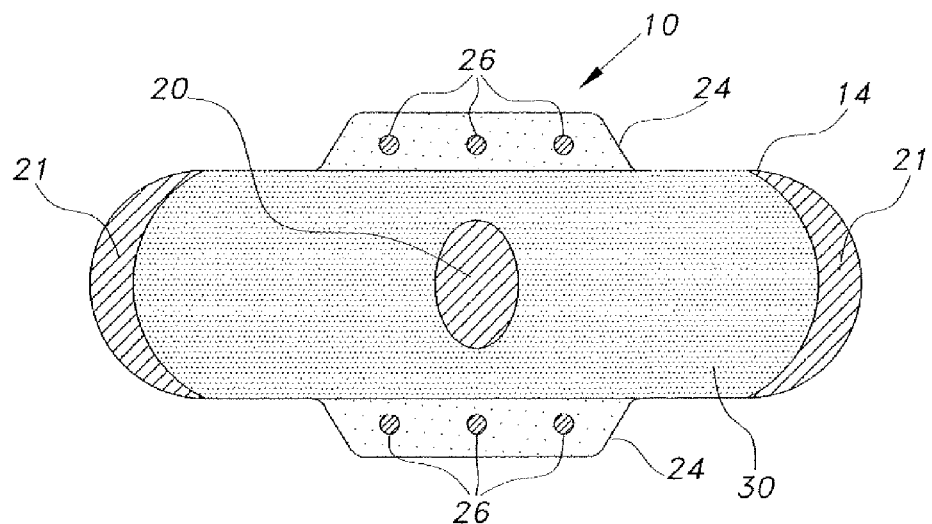
FIG. 4 is a plan view of a further alternative embodiment of a feminine hygiene pad with releasable fastener according to the present invention.

As shown in FIGS. 3 and 4, the feminine hygiene pad 10 may further include a pair of extending wings 24, as is conventionally known, extending from lateral side edges of the lower layer 14. Three hook portions 26 may be secured to each of the wings 24, respectively, for releasable attachment of the wings 24 to the exterior of the undergarment U. Although shown as being similar to the releasable attachments 32 of FIG. 5, it should be understood that three hook portions 26 may vary in relative dimensions, configuration, number, and positioning. Further, as shown in FIG. 5, a central additional elastic element 23 may be provided, the hook portion 20 being mounted on top of the elastic element (as opposed to being secured directly to the lower surface 14). It should be understood that the arrangement of the hook portion being mounted on, or covering, a portion of the elastic element, as shown in the embodiment of FIG. 5, may be applied to any of the various embodiments described herein, such as, for example, that of FIG. 3.

In addition to securement to the undergarment U, the releasable attachments further allow a used feminine hygiene pad 10 to be easily disposed of in a sanitary manner. The hook portions may be used to secure the ends of the lower layer 14 to the material of upper layer 12 when the feminine hygiene pad 10 is rolled up or folded for disposal. Although the use of hygiene pads for menstruation is common, the present pad may also be utilized for incontinence, bladder leakage, or any other purpose or situation in which absorbent hygienic pads and/or garments are used. Additionally, it should be understood that the present pad may be used in combination with diapers, panty liners and the like.

It is to be understood that the present invention is not limited to the embodiments described above, but encompasses any and all embodiments within the scope of the following claims.

I claim:

1. An absorbent article with releasable attachment, comprising:
    an absorbent pad having an absorbent upper layer and a liquid impermeable lower layer;
    a pair of tabs, each of the tabs having a free end and a fixed end, the fixed end being rigidly attached to the lower layer of the absorbent pad adjacent longitudinal ends of the absorbent hygiene pad;
    a hook portion of a hook and loop fastener attached to each of the tabs, the hook portions being adapted for engaging material forming an undergarment, the material forming the undergarment acting in lieu of a corresponding loop portion of a hook and loop fastener to secure the tabs to the undergarment;
    means for releasably securing the lower layer of the absorbent pad directly to an interior surface of the undergarment, wherein the means for releasably securing the lower layer of the absorbent hygiene pad includes a secondary hook portion of a hook and loop fastener attached to the lower layer, wherein the secondary hook portion is positioned substantially centrally on the lower layer of the absorbent pad; and
    at least a pair of elastic elements attached to the lower layer to maintain the absorbent pad in a non-collapsed state, wherein each of the elastic elements has an elongated axis and is disposed longitudinally adjacent to the secondary hook portion thereby sandwiching the secondary hook portion therebetween, whereby the elongated axis of each of the elements is orientated substantially perpendicular to the longitudinal axis of the absorbent pad.

2. The absorbent article as recited in claim 1, wherein said absorbent pad has a pair wings extending from lateral side edges of said hygiene pad.

3. The absorbent article as recited in claim 2, further comprising means for releasably securing the wings to an exterior surface of the undergarment.

4. The absorbent article as recited in claim 1, further comprising means for at least partially limiting movement of the free end of each said tab.

5. The absorbent article as recited in claim 1, wherein each of the elastic elements is attached to the outer surface of the lower layer.

6. The absorbent article as recited in claim 1, further comprising an additional pair of elastic elements, each of the additional pair of elastic elements has an elongated axis and being disposed adjacent to the secondary hook portion and parallel to the longitudinal axis of the pad and thereby sandwiching the secondary hook portion therebetween, wherein the elastic elements substantially surround the secondary hook portion.

7. An absorbent article with releasable attachment, comprising:
    an absorbent pad having a longitudinal axis and an absorbent upper layer and a liquid impermeable lower layer, the lower layer having an outer surface, a front portion, a rear portion, a central portion, and lateral side portions;
    at least a pair of elastic elements attached to the lower layer to maintain the absorbent pad in a non-collapsed state, wherein each of the elastic elements has an elongated axis and is disposed longitudinally adjacent to the central portion thereby sandwiching the central portion therebetween, whereby the elongated axis of each of the elements is orientated substantially perpendicular to the longitudinal axis of the absorbent pad;
    a pair of tabs, each of the tabs having at least one fixed end, the at least one fixed end being rigidly attached to the lower layer of the absorbent pad adjacent longitudinal ends of the absorbent pad; and
    means for releasably securing the tabs to an interior surface of an undergarment to indirectly secure the absorbent pad to the undergarment.

8. The absorbent article as recited in claim 7, wherein said means for releasably securing said tabs to the interior surface of the undergarment comprises a hook portion of a hook and loop fastener, each of the tabs having the hook portion attached thereto, the hook portion of each of the tabs being adapted for engaging material forming the undergarment, the material forming the undergarment acting as a corresponding loop portion of a hook and loop fastener in order to secure the tabs to the undergarment.

9. The absorbent article as recited in claim 8, wherein said absorbent pad has a pair of wings extending from lateral side edges of said pad.

10. The absorbent article as recited in claim 9, further comprising means for releasably securing the wings to an exterior surface of the undergarment.

11. The absorbent article as recited in claim 10, wherein said means for releasably securing the wings to the exterior surface of the undergarment comprises the hook portion of hook and loop fasteners attached to the wings.

12. The absorbent article as recited in claim 7, further comprising an additional pair of elastic elements, each of the additional pair of elastic elements have an elongated axis and being disposed adjacent to the central portion and parallel to the longitudinal axis of the pad and thereby sandwiching the central portion therebetween, wherein the elastic elements substantially surround the central portion.

13. The absorbent article as recited in claim 7, wherein each of the elastic elements is attached to the outer surface of the lower layer.

* * * * *